US012427089B2

(12) United States Patent
Beard et al.

(10) Patent No.: US 12,427,089 B2
(45) Date of Patent: Sep. 30, 2025

(54) CLOSED SYSTEM TRANSFER DEVICE AND VIAL ASSEMBLY MACHINE

(71) Applicant: AMGEN INC., Thousand Oaks, CA (US)

(72) Inventors: Nicholas Beard, Thousand Oaks, CA (US); Julian Jazayeri, Woodland Hills, CA (US); David Selpa, Thousand Oaks, CA (US); Ryan David Selve, Canyon Country, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 18/692,002

(22) PCT Filed: Sep. 27, 2022

(86) PCT No.: PCT/US2022/044794
§ 371 (c)(1),
(2) Date: Mar. 14, 2024

(87) PCT Pub. No.: WO2023/055699
PCT Pub. Date: Apr. 6, 2023

(65) Prior Publication Data
US 2024/0285472 A1    Aug. 29, 2024

Related U.S. Application Data

(60) Provisional application No. 63/249,337, filed on Sep. 28, 2021.

(51) Int. Cl.
*A61J 1/20* (2006.01)

(52) U.S. Cl.
CPC ...................................... *A61J 1/20* (2013.01)

(58) Field of Classification Search
CPC ................................. A61J 1/20; A61J 1/2089
(Continued)

(56) References Cited

U.S. PATENT DOCUMENTS 6,360,794 B1    3/2002  Turner
8,225,824 B2    7/2012  Eliuk et al.
(Continued)

OTHER PUBLICATIONS

International Search Report for Application No. PCT/US2022/044794 dated Dec. 16, 2022.
(Continued)

*Primary Examiner* — Timothy L Maust
(74) *Attorney, Agent, or Firm* — MARSHALL, GERSTEIN & BORUN LLP; Michael P. Furmanek

(57) ABSTRACT

A closed system transfer device (CSTD) and vial assembly machine includes a linear travel assembly including a linear mount, and an actuator operably coupled to the linear mount. The linear mount is movable in an axial direction between a first position and a second position spaced from the first position. A CSTD fixture is configured to be removably coupleable to the linear mount. A vial mount is disposed adjacent to a portion of the linear travel assembly. A vial fixture is configured to be removably coupleable to the vial mount. The vial fixture is sized to hold a vial in axial alignment with a portion of the CSTD fixture when the vial fixture is coupled to the vial mount and the CSTD fixture is coupled to the linear mount. When the linear mount moves from the first position to the second position, the linear mount moves relative to the vial mount.

17 Claims, 16 Drawing Sheets

(58) Field of Classification Search
USPC .................................. 604/403–415; 141/329
See application file for complete search history.

(56) References Cited

U.S. PATENT DOCUMENTS

| | | | | |
|---|---|---|---|---|
| 8,267,129 | B2* | 9/2012 | Doherty | A61J 1/2096 |
| | | | | 141/330 |
| 8,807,177 | B2* | 8/2014 | Strangis | B63C 9/0005 |
| | | | | 604/416 |
| 9,173,816 | B2 | 11/2015 | Reinhardt et al. | |
| 9,433,558 | B2* | 9/2016 | Okuda | A61J 3/002 |
| 9,868,553 | B2* | 1/2018 | Matsukuma | B65B 3/003 |
| 12,029,704 | B2* | 7/2024 | Bianco | B25J 9/06 |
| 2015/0251781 | A1 | 9/2015 | Matsukuma et al. | |

OTHER PUBLICATIONS

Written Opinion for Application No. PCT/US2022/044794 dated Dec. 16, 2022.

* cited by examiner

CLOSED SYSTEM TRANSFER DEVICE AND VIAL ASSEMBLY MACHINE

This is the United States national phase of International Patent Application No. PCT/US2022/044794, filed Sep. 27, 2022, which claims priority to U.S. Provisional Patent Application No. 63/249,337, filed Sep. 28, 2021, the entire contents of each of which are hereby incorporated by reference herein.

FIELD OF DISCLOSURE

The present disclosure relates to assembling a closed system transfer device (CSTD) and a vial, and more particularly, to a machine that assembles a CSTD and a vial.

BACKGROUND

A closed system transfer device (CSTD) is a device designed to transfer drugs between vials and syringes, where traditional transferring of drugs is not viable. For example, CSTDs for hazardous pharmaceuticals are attached to vials containing the drug to capture the drug product and sealing the system to protect the patient and practitioner from the hazardous contents. Typically, the CSTD is manually secured to a top portion of the vial containing a drug. A vial spike of the CSTD pierces a stopper disposed at the opening of the vial to connect the CSTD and the contents of the vial. Assembly of a CSTD to a drug vial may be arduous and installation can lead to stopper fragmentation within the drug vial or coring, thereby contaminating the drug and/or clogging the CSTD spike.

SUMMARY

In accordance with a first aspect, a closed system transfer device (CSTD) and vial assembly machine may include a linear travel assembly including a linear mount and an actuator operably coupled to the linear mount. The linear mount may be movable in an axial direction between a first position and a second position spaced from the first position. The machine may include a CSTD fixture configured to be removably coupleable to the linear mount. A vial mount may be disposed adjacent to a portion of the linear travel assembly. A vial fixture may be configured to be removably coupleable to the vial mount. The vial fixture may be sized to hold a vial in axial alignment with a portion of the CSTD fixture when the vial fixture is coupled to the vial mount and the CSTD fixture is coupled to the linear mount. When the linear mount moves from the first position to the second position, the linear mount may move relative to the vial mount.

In accordance with a second aspect, a method of assembling a closed system transfer device (CSTD) with a vial may include attaching a CSTD fixture to a linear mount of a linear travel assembly of a machine. The linear travel assembly may include the linear mount and an actuator operably coupled with the linear mount. The linear mount may be movable in an axial direction between a first position and a second position spaced from the first position. The method may include attaching a CSTD to the CSTD fixture, and attaching a vial fixture to a vial mount of the machine. The vial mount may be disposed adjacent to a portion of the linear travel assembly. The method may include attaching a vial to the vial fixture. The vial may be in axial alignment with a portion of the CSTD. The method may include activating the linear travel assembly to move the linear mount from the first position to the second position. Further, the method may include engaging a portion of the CSTD with the vial when the linear mount is in the second position.

In further accordance with any one of the first and second aspects, a CSTD and vial assembly machine and/or a method of assembling a CSTD with a vial may include any one or more of the following forms.

In one form, a controller communicatively may be coupled with the linear travel assembly.

In some forms, the controller may be programmed to move the linear mount to the first position and to move the linear mount to the second position.

In another form, the controller may be communicatively coupled to the actuator of the linear travel assembly to change position of the linear mount.

In some forms, a rotary assembly may include the vial mount and an actuator operably coupled with the vial mount to rotate the vial mount in one or more directions.

In one example, the controller may be communicatively coupled with the rotary assembly.

In another example, the controller may be programmed to receive a first rotation signal to rotate the vial mount in a first direction.

In another example, the controller may be programmed to receive a second rotation signal to rotate the vial mount in the first direction and the second direction.

In other examples, the controller may be communicatively coupled to the actuator of the rotary assembly to rotate the vial mount in one or more directions.

In some examples, the controller may be programmed to receive a first signal to operate the actuator of the linear travel assembly to move the linear mount at a first speed.

In another example, the controller may be programmed to receive a second signal to move the linear mount at a second speed different than the first speed.

In one form, the controller may be programmed to receive a first positioning signal to move the linear mount to the first position.

In another form, the controller may be programmed to receive a second positioning signal to move the linear mount from the first position to the second position.

In other forms, the controller may be programmed to move the linear mount to a third position spaced from the first position and the second position.

In some examples, the CSTD fixture may be selected from a plurality of available and distinct CSTD fixtures.

In one example, the vial fixture may be selected from a plurality of available and distinct vial fixtures.

In another example, the method may include receiving, via a controller, a first position signal to move the linear mount to the first position.

In another example, the controller may be communicatively coupled to the actuator of the linear travel assembly.

In one form, the method may include receiving, via the controller, a second position signal to move the linear mount to the second position.

In another form, the method may include receiving, via the controller, a first speed signal to move the linear mount at a first speed.

In other forms, the method may include receiving, via the controller, a second speed signal to move the linear mount at a second speed.

In one example, the second speed may be greater than the first speed.

In some examples, attaching the vial fixture to the vial mount may include securing the vial fixture to a rotary assembly of the machine.

In one example, the rotary assembly may include the vial mount and an actuator operably coupled to the vial mount.

In one example, the method may include receiving, via the controller, a first rotation signal to rotate the vial fixture in a first direction.

In one example, the controller may be communicatively coupled to the actuator of the rotary assembly.

In another example, the method may include receiving, via the controller, a second rotation signal to rotate the vial fixture in the first direction and the second direction, opposite the first direction.

In one form, the method may include selecting the CSTD from a plurality of available and distinct CSTDs.

In another form, the method may include selecting the CSTD fixture from a plurality of available and distinct CSTD fixtures.

In other forms, the method may include selecting the vial from a plurality of available and distinct vials.

In some examples, the method may include selecting the vial fixture from a plurality of available and distinct vial fixtures.

In one example, the method may include selecting a vial insert from a plurality of available and distinct vial inserts.

In another example, the method may include removing the CSTD and vial after the CSTD engages the vial and coupling the CSTD with the vial.

DETAILED DESCRIPTION

Figure 1:
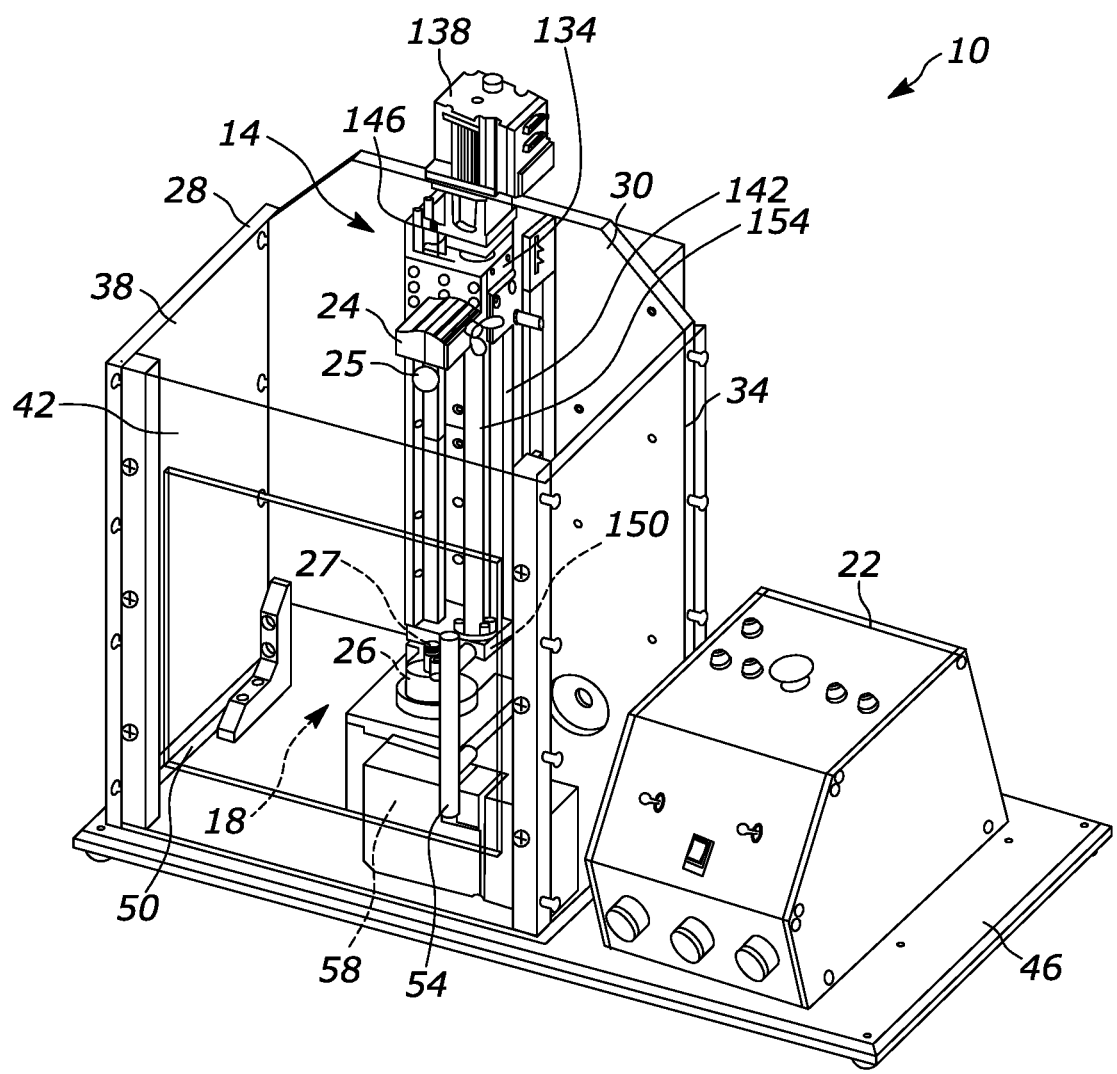
FIG. 1 is a perspective view of a closed system transfer device (CSTD) and vial assembly machine assembled in accordance with the teachings of the present disclosure.

A closed system transfer device (CSTD) and vial assembly machine 10 in FIG. 1 assembles a CSTD onto a vial with a stopper. The machine 10 can apply a CSTD in either slow or fast speed and choose whether the vial is stationary, rotating in one direction, or rotating back and forth. The machine 10 is also adapted to receive a number of different CSTD and vial fixtures to assemble a variety of CSTD and vial combinations. As used herein, the terms "assemble" and "assembly" may refer to any type of coupling of the CSTD and vial. The method and machine described herein may assemble CSTDs and vials for a variety of reasons, for example, testing quality control of samples and/or use of the assembled CSTD and vial by a healthcare provider for patient-use. Coring may be affected by various user-controlled variables, such as, for example, speed, force, and rotation applied by the user when manually assembling the CSTD or vial. The disclosed method and machine may provide a repeatable method to simulate different variables and/or techniques employed by a user to test the components and provide input for component designers. In some examples, the disclosed machine and method may help designers identify techniques for assembling a CSTD and vial that reduce the likelihood of coring. In other examples, the disclosed machine and method may provide insight for designing the CSTD, vial, or other components to reduce instances of coring. With these findings, assembly of these components via machine or by hand may help minimize coring.

The CSTD and vial assembly machine 10 of FIG. 1 includes a linear travel assembly 14, a rotary assembly 18, and a controller 22 operably coupled to the linear travel and rotary assemblies 14, 18. The linear travel assembly 14 is arranged to move a CSTD in an axial direction toward a vial mounted to the rotary assembly 18. The controller 22 of the machine 10 operates the linear travel assembly 14 to move a CSTD fixture 24 carrying a CSTD 25 toward a vial fixture 26 carrying a vial 27 to couple the CSTD 25 to the vial 27. The controller 22 may be programmed to move the CSTD 25 to different locations and at different speeds, and to rotate the vial 27 in one or more directions about the axis upon which the CSTD travels as the CSTD 25 moves toward the vial 27 during assembly. The controller 22 is communicatively coupled to the linear and rotary assemblies 14, 18 via wired or wireless connections. The machine 10 may be powered using a separate or integrated power supply.

The linear travel assembly 14 and rotary assembly 18 are enclosed within a housing 28 of the machine 10. The housing 28 includes a back wall 30, first and second side walls 34, 38, and a front wall 42 attached to a platform 46. The controller 22 is adjacent to the first side wall 34 of the housing 28 and mounted to or otherwise disposed on the same platform 46. The linear travel assembly 14 is coupled to the back wall 30, and the rotary assembly 18 is disposed adjacent to a portion of the linear travel assembly 14 (e.g., a lower portion) and attached to the platform 46. The linear travel assembly 14 and rotary travel assembly 18 are accessible by opening a door 50 attached to the front wall 42. The door 50 includes a handle 54 and a secure lock 58 operably coupled to the controller 22 such that the door 50 remains closed and locked during assembly of the CSTD 25 and vial 27 and when the machine 10 is powered off.

Figure 3:
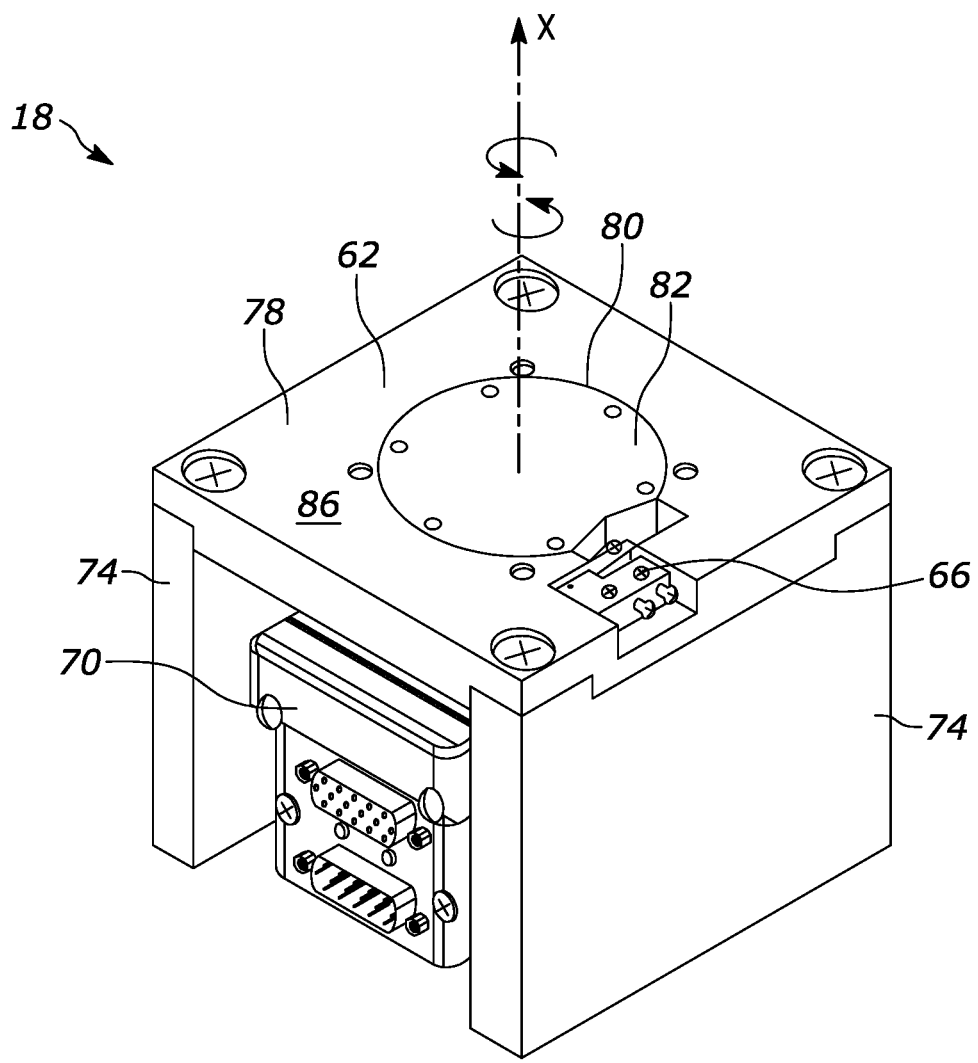
FIG. 3 is a perspective view of a rotary assembly of the machine of FIG. 1.
Figure 4:
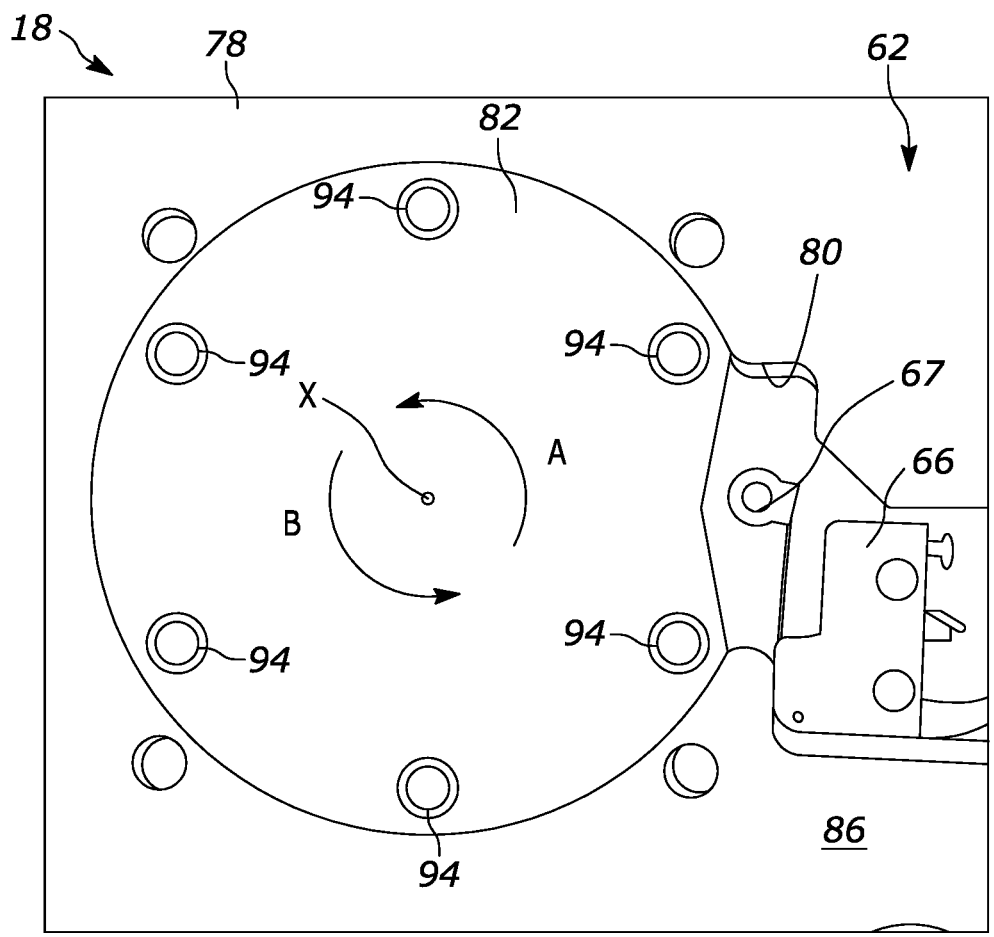
FIG. 4 is a top view of the rotary assembly of the machine of FIG. 3.

In FIGS. 3 and 4, the rotary assembly 18 includes a vial mount 62, a switch 66, an actuator 70, and support walls 74. The vial mount 62 includes a platform 78 defining a recess 80 and a rotatable base 82 disposed in, and rotatable relative to, a circular portion of the recess 80. The platform 78 is arranged to support the rotatable base 82 while allowing a connection between the actuator 70 and the rotatable base 82. The rotatable base 82 sits in the recess 80 and is flush with a top surface 86 of the platform 78 to provide the vial mount 62 with a generally planar top surface. The rotatable base 82 is circular and rotates on a thrust ball bearing disposed between a bottom planar surface of the recess 80 and the rotatable base 82. A connector is disposed on an opposite side of the rotatable base 82 to connect with a rod of the actuator 70. The connector of the base 82 and/or the rod of the actuator 70 extends through a hole formed in the bottom planar surface of the circular recess 80 of the platform 78 to couple the actuator 70 and the rotatable base 82. The actuator 70 is arranged to rotate the rotatable base 82 about an X axis in a first direction A, a second direction B, or alternating between the first and second directions A, B. In the disclosed embodiment, the X axis is substantially coaxial with an axis of travel of the CSTD during assembly. The actuator 70 may also be arranged to be idle or locked so that the rotatable base 82 does not rotate at all.

Figure 5:
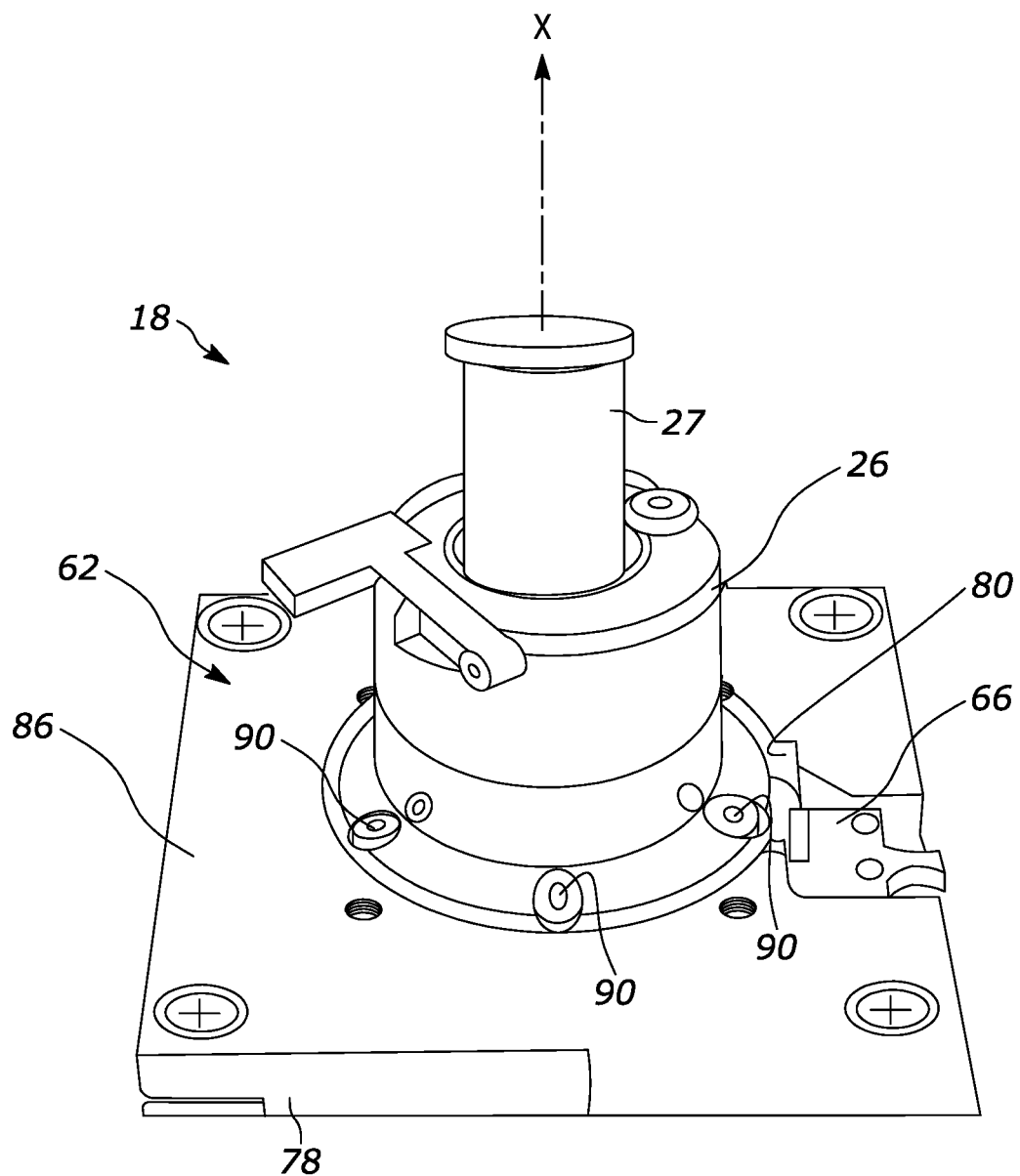
FIG. 5 is a perspective view of a vial fixture holding a vial and secured to the rotary assembly of FIG. 3.

FIG. 5 illustrates the vial fixture 26 secured to the vial mount 62 and holding the vial 27. A plurality of fasteners 90 secure the vial fixture 26 to the vial mount 62 via a plurality of apertures 94 (FIGS. 3 and 5) formed in the rotatable base 82. The vial fixture 26 is sized to hold the vial 27 in axial alignment with the X axis. When the vial 27 and vial fixture 26 are mounted to the vial mount 62, the vial 27 aligns with the X axis and a portion of the CSTD fixture 24 when the CSTD fixture 24 is mounted to the linear travel assembly 14. The vial fixture 26 is sized to receive a particularly sized vial 27, and may be selected from a plurality of available and distinct vial fixtures 26 for holding various sized vials 27. Each of the plurality of vial fixtures 26 is arranged to mount to the rotary assembly 18 in a similar or different manner.

The switch 66 is a precision snap-acting switch, and is disposed in a different portion of the recess 80 of the platform 78. The switch 66 is in a home position, as shown in FIG. 4, and not in contact with the rotatable base 82. When the rotatable base 82 swings into contact with a trigger arm 67 of the switch 66, the switch 66 registers the rotation of the rotatable base 82.

Figure 6:
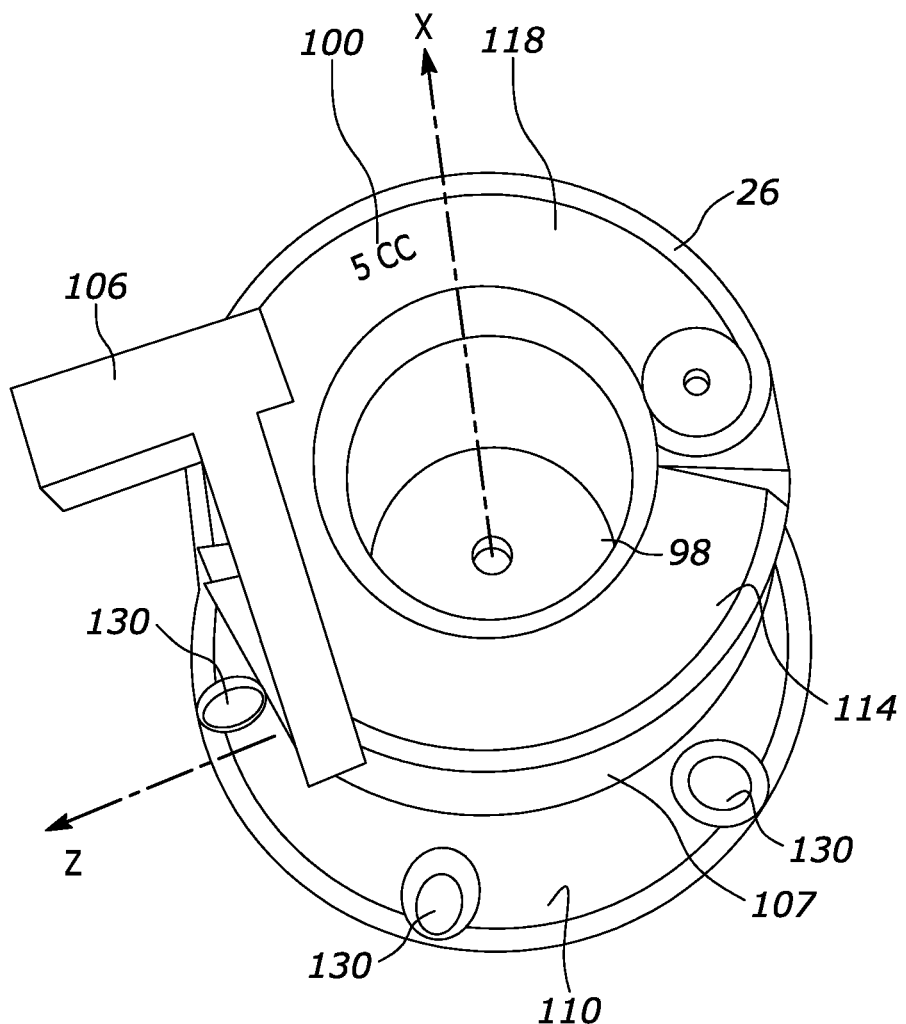
FIG. 6 is a top, perspective view of the vial fixture of FIG. 5.
Figure 7:
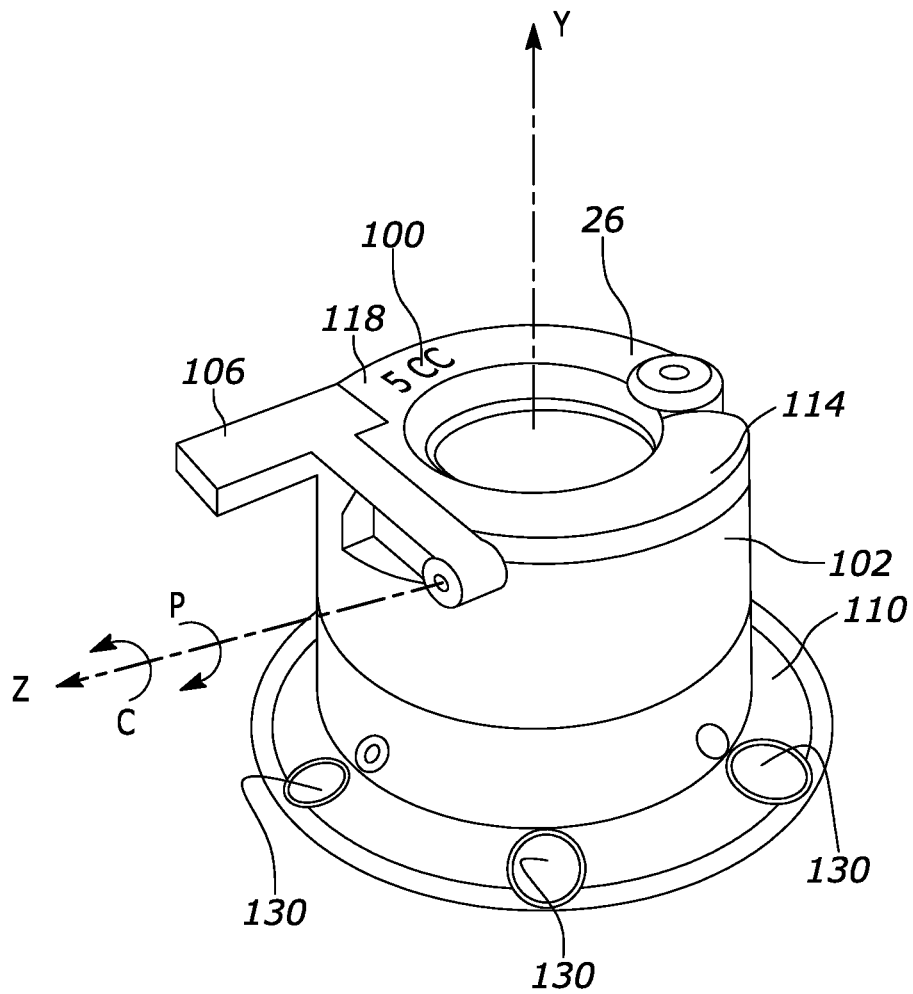
FIG. 7 is a side, perspective view of the vial fixture of FIG. 6.
Figure 8:
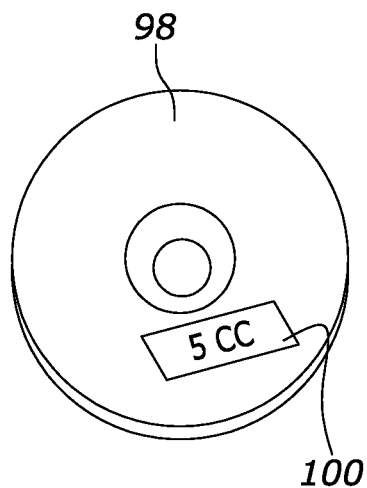
FIG. 8 is a top, perspective view of an insert of the vial fixture of FIG. 6.

Turning to FIGS. 6-8, an example vial fixture 26 and insert accessory 98 are illustrated. The vial fixture 26 includes a body 102, a handle 106, and a flange 110 at a base of the body 102 to connect the vial fixture 26 to the rotary assembly 18. The body 102 includes first and second halves 114, 118 that rotate relative a hinge 122 to open and close. As shown in FIGS. 6 and 7, the first and second halves 114, 118 define a cylindrical bore 126 when the first and second halves 114, 118 are closed and secured together with the handle 106 in a locked position. The insert accessory 98 of FIG. 8 is sized according to the corresponding size of the fixture 26, and is placed inside the bore 126 to provide added height to the vial 27 when mounted to the rotary assembly 18. The insert 98 lifts the vial 27 up when disposed in the fixture 26 to ensure the vial 27 is in proper positioning in the machine 10 for coupling with the CSTD 25. The insert 98 thereby facilitates the insertion of a spike of the CSTD 25 into and/or through the vial stopper. One or more inserts 98 of the same or different sizes may be selected and may be inserted into the vial fixture 26. However, if the vial 27 is lifted too high, the spiking of the stopper may cause the glass of the vial to burst.

In an open position, the first and second halves 114, 118 of the vial fixture 26 may be slightly or largely separated to widen the opening of the cylindrical bore 126 to more easily receive a vial 27. When the fixture 26 is in the locked position, the first and second halves 114, 118 are pulled together to securely hold the vial 27 in the cylindrical bore 126 of the vial fixture 26. The handle 106 is rotatably coupled to the first half 114 and tightens the first and second halves 114, 118 around a vial 27 when the handle 106 is disposed in a groove formed in a top portion of the second half 118. To open the first and second halves 114, 118 to place the vial 27 into or remove the vial 27 from the fixture 26, the handle 106 may be lifted away from the second half 118 by rotating the handle 106 about a pivot axis Z (shown in FIGS. 6 and 7), perpendicular relative to the X axis of the fixture 26. The flange 110 includes a plurality of bores 130 spaced about the circumference of the flange 110 to receive the fasteners 90 for coupling the vial fixture 26 to the rotatable base 82 of the rotary assembly 18. Once fastened to the rotatable base 82, the vial fixture 26 rotates about the X axis when the rotatable base 82 rotates.

As shown in FIGS. 6-8, the vial fixture 26 and the insert 98 both include labels 100 indicating that they are intended for use with a 5 cc vial. These labels 100 are example labels to identify the corresponding fixture 26 and insert 98 when assembling a 5 cc vial with a CSTD using the machine 10. Other fixtures 26 of varying sizes and corresponding inserts 98 may be selected based on the size of the vial for assembly. For example, other fixtures similar to the fixture 26 illustrated and described herein may be sized to receive 6R vials, 10 cc vials, or any other vials. In yet another example, the fixture 26 may be modified with different inserts to receive vials of various sizes.

Figure 2:
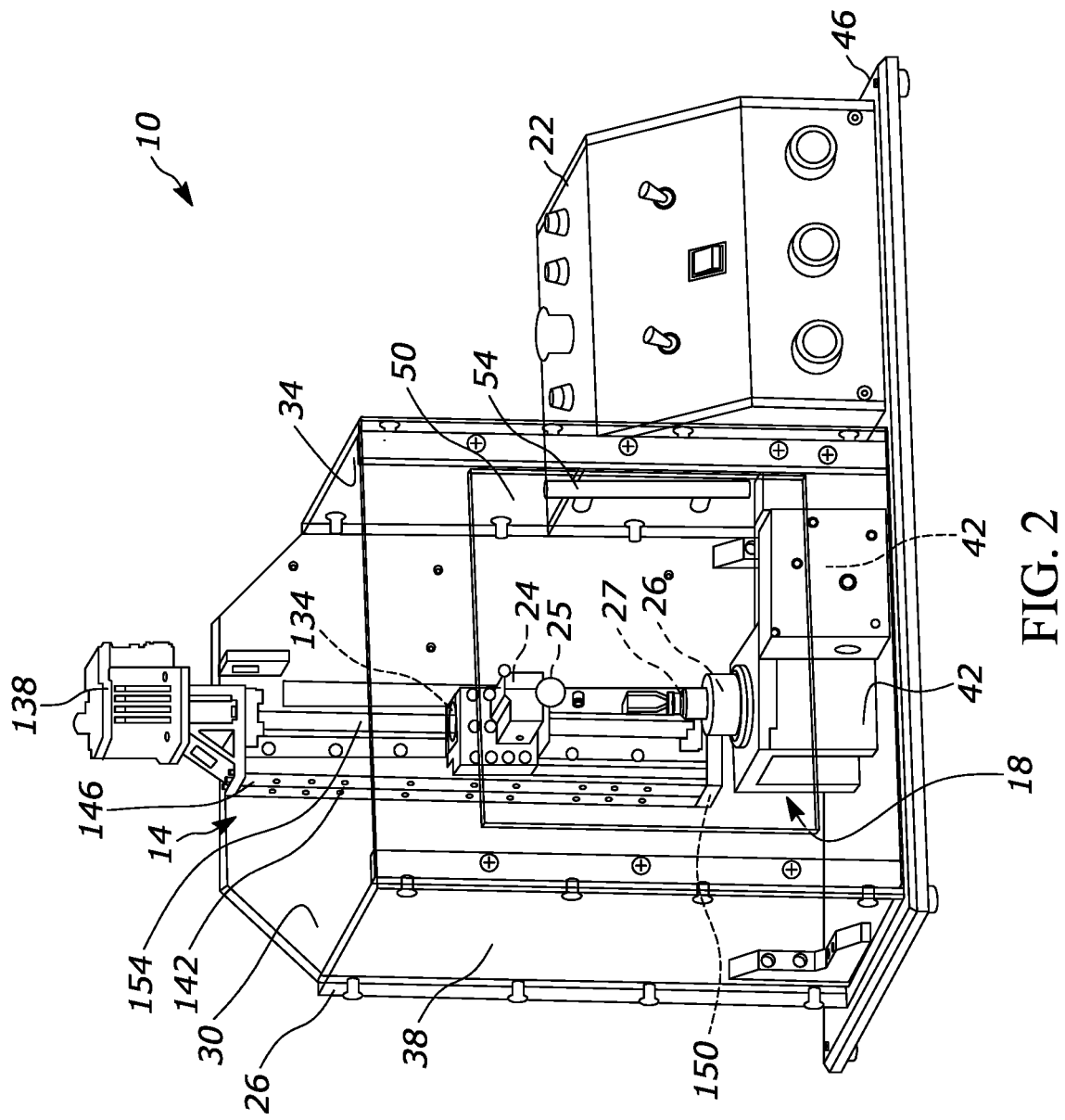
FIG. 2 is a front view of the machine of FIG. 1.

Turning back to FIGS. 1 and 2, the linear travel assembly 14 includes a linear mount 134 and an actuator 138 operably coupled to the linear mount 134. The linear mount 134 is movable in an axial direction between an initial position, as shown in FIG. 1, a first position, as shown in FIG. 2, and a second position (not shown) that is spaced from the initial and first positions and adjacent to the rotary assembly 18. The first position is located between the initial and second positions. Specifically, the linear mount 134 is slidably coupled to a track 142 extending from a first end 146 to a second end 150. In the first position illustrated in FIG. 2, the linear mount 134 is disposed approximately at a midpoint location of the track 142. The actuator 138 is disposed on a support attached to the first end 146 of the track 142, and is coupled to a slide rod 154. The actuator 138 operates the slide rod 154 to move the linear mount 134 along the track 142 between initial, first, and second positions. The vial mount 62 is disposed adjacent to the second end 150 of the track 142 of the linear travel assembly 14 such that as the CSTD fixture 24 carrying the CSTD 25 moves toward the second end 150 of the track 142 and into the second position, the CSTD 25 engages the vial 27 secured in the vial mount 62. As will be discussed further below, the controller 22 is communicatively coupled to the actuator 138 of the linear travel assembly 14 to control the speed and positioning of the linear mount 134 relative to the rotary assembly 18. The controller 22 is also communicatively coupled to the rotary assembly 18 to selectively control the rotation of the vial mount 62.

Figure 10:
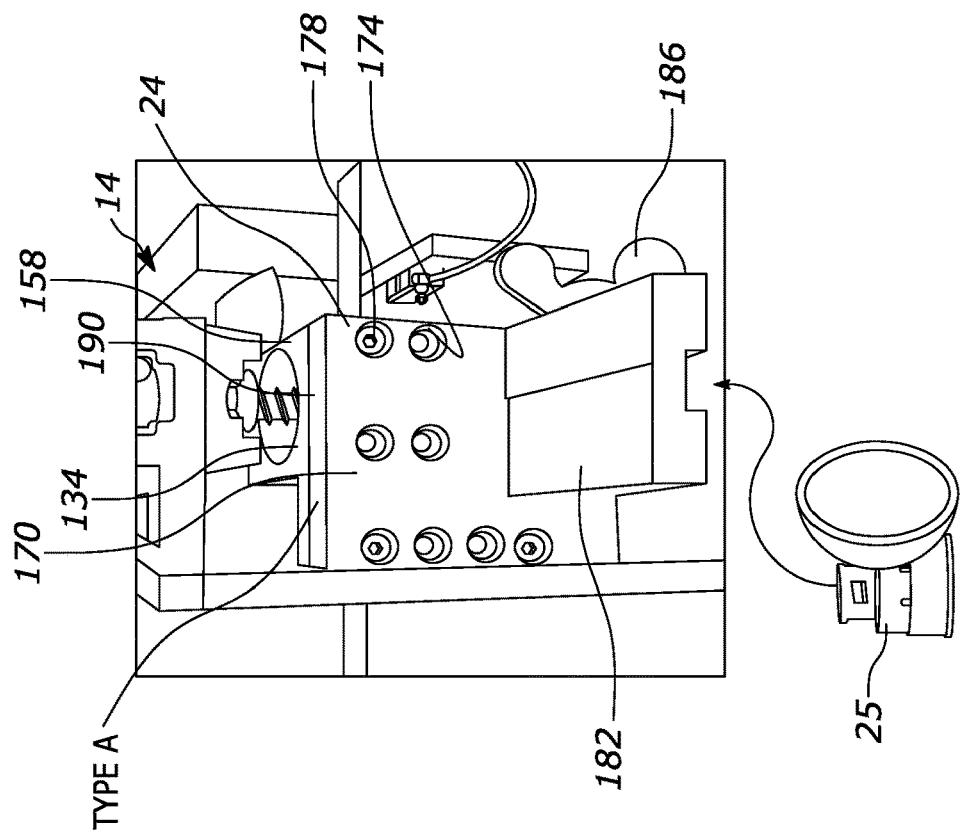
FIG. 10 is a front view of a CSTD fixture holding a CSTD and secured to the linear mount of FIG. 9.
Figure 9:
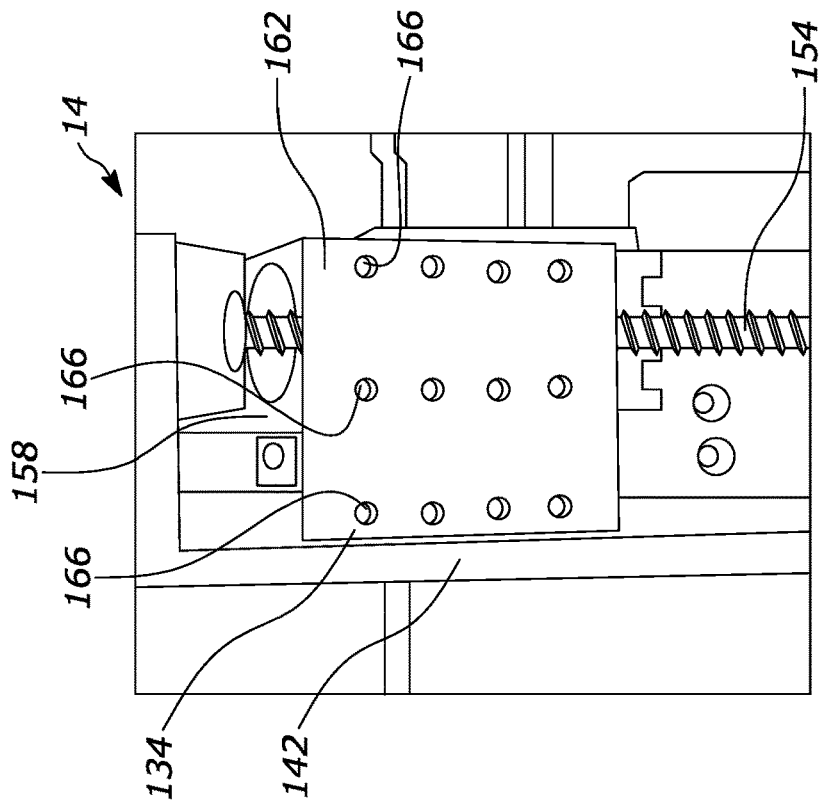
FIG. 9 is a front view of a linear mount of a linear travel assembly of the machine of FIG. 1.

In FIG. 9, the linear mount 134 of the travel assembly 14 is illustrated. The linear mount 134 includes a body 158 and mounting platform 162 attached to the body 158. The slide rod 154 extends through a bore in the body 158, and is threadably coupled to the bore via internal threads formed in the bore. So configured, the actuator 138 of the linear travel assembly 14 rotates the slide rod 154 about its longitudinal axis. The threaded connection between the bore of the body 158 and the slide rod 154 converts the rotational motion of the actuator 138 to a linear motion of the linear mount 134 along the track 142. The platform 162 includes a plurality of apertures 166 for securing the CSTD fixture 24 to the linear mount 134, as shown in FIG. 10. The platform 162 includes three columns of four apertures 166. However, in other examples, the linear mount 134 may include a different arrangement of apertures or method of securing the CSTD fixture 24 to the linear mount 134. While the present embodiment utilizes a threaded connection between the slide rod 154 and the body 158 to effectuate linear travel of the linear mount 134, other versions can effectuate linear travel of the linear mount 134 in different ways such as through the use of hydraulics, rack and pinion gearing, etc.

Figure 11:
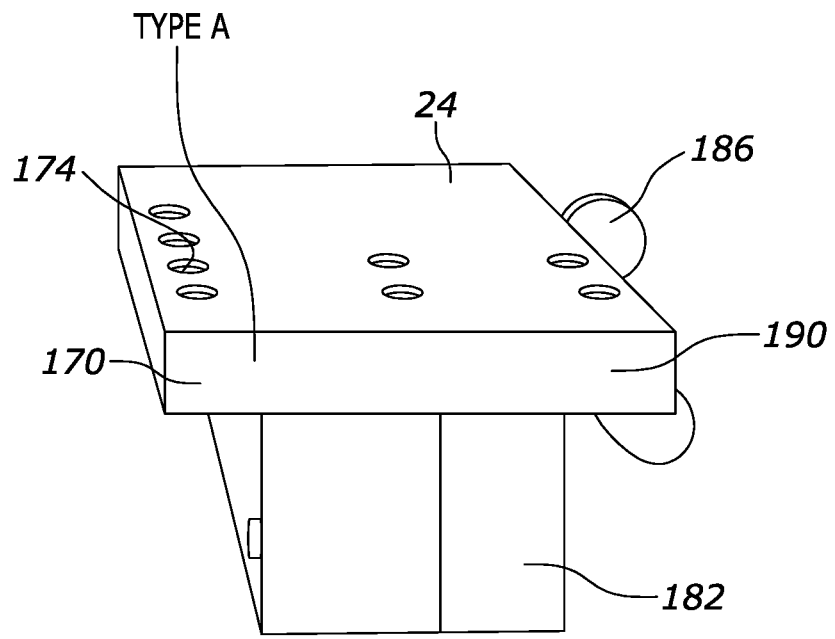
FIG. 11 is a top view of the CSTD fixture of FIG. 10.
Figure 12:
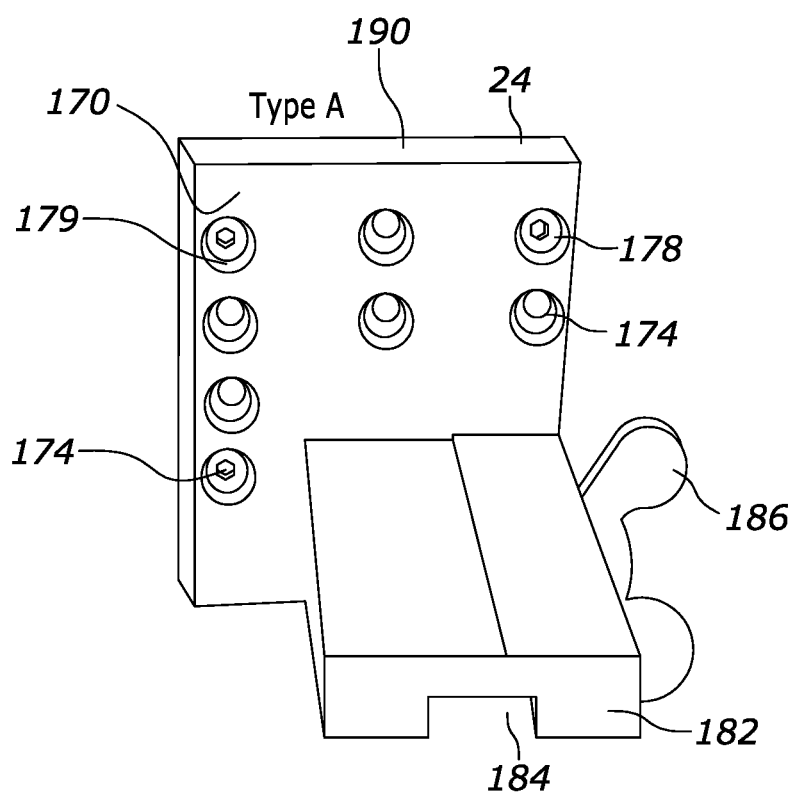
FIG. 12 is a front, perspective view of the CSTD fixture of FIG. 11.

The CSTD fixture 24 is illustrated in FIGS. 10-12 and includes a plate 170 shaped for sitting flush against the platform 162 of the linear mount 134. The plate 170 of the CSTD fixture 24 includes a plurality of bores 174 extending through the plate and sized to receive a plurality of fasteners 178 that secure the plate 170 of the fixture 24 to the platform 162 of the linear mount 134. The CSTD fixture 24 includes a mounting arm 182 extending perpendicularly from a surface of the plate 170. An example CSTD 25 is fastened to a receiving opening 184 (such as, for example, an aperture, bore, slot, or groove) formed in the arm 182 such that a portion of the CSTD 25 is aligned with a vial 27 when the vial 27 is coupled to the vial mount 62. A wing nut 186 secures the CSTD 25 in place so that the linear mount 134 carries the CSTD 25 secured to the CSTD fixture 24 when operating the machine 10. The CSTD fixture 24 receives and frictionally engages the top portion of the CSTD 25 by adjusting the friction point with the wing nut 186. However, the wing nut 186 should be loose enough so that the CSTD 25 separates from the fixture 24 when the CSTD 25 couples with the stopper of the vial 27. Other coupling mechanisms are possible, and may include pneumatics to turn on/turn off the engagement between the CSTD 25 and the CSTD fixture 24.

Like the vial 27 and the vial fixture 26 of the rotary assembly 14, the CSTD 25 and CSTD fixture 24 are removable from the linear assembly 14. The CSTD 25 may be removed from the CSTD fixture 24 by rotating the wing nut 186 to loosen the CSTD 25 from the fixture 24, and the CSTD fixture 24 may be removed from the linear mount 134 by removing the fasteners 178.

As shown in FIGS. 10-12, the CSTD fixture 24 is labeled for a Type and Size 190 CSTD 25 for assembly with a particular size vial 27. The example label 190 identifies the size and type of the fixture 24 when assembling the vial 27 with the CSTD 25. Other fixtures 24 of varying sizes and types may be provided and selected based on the type of CSTD 25 and/or size of the vial 27. For example, other fixtures similar to the fixture 24 illustrated and described herein may be sized to receive BD PhaSeal, Tevadaptor, ChemoClave, and Equashield CSTDs. In yet another example, the fixture 24 may be modified with different inserts to receive various types of CSTDs.

Figure 13:
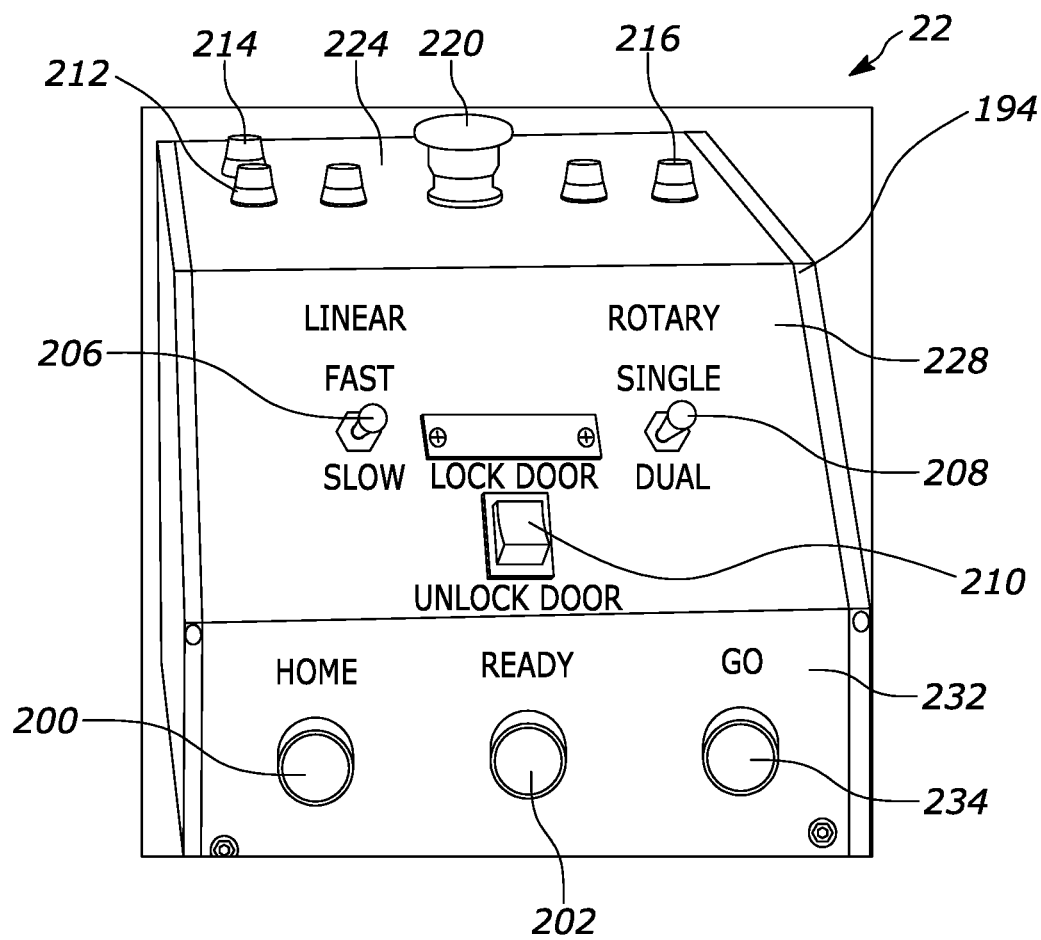
FIG. 13 is a front view of a control box of the machine of FIG. 1.

The controller 22 is shown generally in FIG. 13 and is communicatively coupled with the linear travel assembly 14 and rotary travel assembly 18 of the machine 14. The controller 22 is housed in a control box 194 and is programmed to receive a plurality of different commands and inputs to operate the machine 10. The control box 194 includes a plurality of buttons 200, 202, 204, 220 and switches 206, 208, 210 for operating and controlling the linear travel assembly 14, the rotary assembly 18, and the door 54. The control box 194 also includes status lights 212, 214, 216 to communicate to the operator various warnings or statuses of the machine 10. While the control box 194 separately houses the controller 22 and is disposed adjacent to the housing 28 of the machine 10, in another example, the linear travel assembly 14, rotary assembly 18, and controller 22 may be enclosed by the same housing 28 such that the controller 22 is accessible by a user interface, such as a touch-screen, attached or incorporated into one of the plurality of walls of the machine 10. An operator may choose the desired settings using the touch-screen to set a desired assembly configuration.

The plurality of status lights 212, 214, 216 and an emergency stop button 220 are disposed on a top surface 224 of the control box 194. The controller 22 is programmed to communicate (i.e., receive and transmit signals) with both the linear travel assembly 14 and the rotary assembly 18 and turn on/off status lights 212, 214, 216 and/or alarms based on feedback from each assembly 14, 18. The controller 22 operates a first status light 212 to indicate whether the rotary assembly 18 is powered on or off, and a second status light 214 to indicate whether the linear travel assembly 14 is powered on or off. The controller 22 may operate other status lights 216 to indicate whether certain features of the machine are inactive, active, or malfunctioning. Centered on the top surface 224 of the control box 194 is the emergency stop button 220 that, when pressed, signals to the controller 22 to stop all actuators 70, 138 of the machine 10.

A set of control switches 206, 208 for the machine 10 are disposed on an angled surface 228 of the control box 194, and operate both the linear travel assembly 14 and the rotary assembly 18. The controller 22 is programmed to communicate with the actuator 138 of the linear travel assembly 14 to change position and travel speed of the linear mount 134. The controller 22 is programmed to receive a first signal, via a first switch 206, to operate the actuator 138 of the linear travel assembly 14 to move the linear mount 134 at the first speed. The controller 22 is also programmed to receive a second signal, via the first switch 206, to move the linear mount 134 at the second speed. The first switch 206 is therefore a three-way switch that sets the speed of the linear mount 134 between slow, neutral or off, or fast speeds. In one example, a first speed may be in a range of approximately 0.02 m/s to approximately 0.04 m/s, a range of approximately 0.025 m/s to approximately 0.035 m/s, and a range of approximately 0.03 m/s to approximately 0.032 m/s. An operator may set the speed by pushing the first switch in a first direction from center (e.g., upwards in FIG. 13) to set a fast speed. The controller 22 receives this setting and transmits a signal to the actuator 138 of the linear travel assembly 14 to move the linear mount 134 at that set fast speed. The operator may instead set the speed by pushing the first switch 206 in a second direction from center (e.g., downwards) to set a slow speed. In one example, a first speed may be in a range of approximately 0.009 m/s to approximately 0.02 m/s, a range of approximately 0.01 m/s to approximately 0.018 m/s, and a range of approximately 0.013 m/s to approximately 0.016 m/s. The controller 22 receives this setting and transmits a signal to the actuator 138 to move the linear mount 134 at the set slow speed. However, in other examples, the first switch 206 may instead be a rotary knob for adjusting the speed of the linear mount 134 between a larger range of speeds.

A second switch 208 of the set of control switches on the angled surface 228 of the control box 194 sets the rotation of the rotary assembly 18. The controller 22 is communicatively coupled with the rotary assembly 18 and is programmed to receive a first rotation signal to rotate the vial mount 62 in a first direction, and to receive a second rotation signal to rotate the vial mount 62 in the first direction and the second direction. In a centered or neutral position (shown in FIG. 13), the actuator 70 of the rotary assembly 18 does not actuate the rotatable base 82 of the vial mount 62. An operator may set the rotation of the rotary assembly 18 in a single direction by pushing the switch 208 in a first direction (e.g., upwards in FIG. 13). The controller 22 receives this setting and transmits a signal to the actuator 70 of the rotary assembly 18 to rotate in one direction. The operator may instead set the rotation of the rotary assembly 18 in a dual direction setting by pushing the switch 208 in a second direction (e.g., downwards). The controller 22 receives this setting and transmits a signal to the actuator 70 to rotate in two directions. So configured, the actuator 70 rotates the rotatable base 82 of the vial mount 62, and therefore the vial fixture 24, about the X axis. When the vial mount 62 is set to rotate in two directions, the rotatable base 82 alternates rotation about the X axis. However, in other examples, the second switch 208 may be a rotary knob for setting a speed as well as a direction of rotation of the vial mount 62. In one example, a rotational speed of the rotatable base 82, in either one direction or two directions, may be in a range of approximately 80 RPM to approximately 100 RPM, a range of approximately 85 RPM to approximately 95 RPM, and a range of approximately 88 RPM to approximately 92 RPM.

The set of control switches 206, 208 control speed of the linear mount 134 and rotation of the vial mount 62 to mimic the movements of a typical operator when manually securing a CSTD to a vial. The various speeds of the linear mount 134 may be similar to various forces applied when securing the CSTD to the vial. Either the first or second settings of the rotary assembly 18 may be similar to a twisting motion of a person when manually assembling the CSTD to a vial. A combination of both force to and torque applied when engaging the CSTD and vial may help determine the causes of coring, and may help determine the appropriate speed and/or rotation to reduce instances of coring.

Finally, a third switch 210 on the angled surface 228 of the control box 194 may be operated to control the door lock 58 of the machine 10. When the third switch 210 is in an unlocked position (e.g., bottom of switch pressed down), the controller 22 signals to the door lock 58 to unlock, permitting an operator to open the door 50 and access the linear travel and rotary assemblies 14, 18. When the third switch (e.g., top of switch pressed down) is in a locked position, the controller 22 signals to the door lock 58 to lock the door 50. The controller 22 may be programmed to automatically lock the door 50 before or after certain controls are set and actions taken. In one example, the controller 22 may be programmed to inhibit any operation of the machine 10 at various stages of using the machine 10 unless the door 50 is fully closed and the lock 58 is activated.

Figure 14:
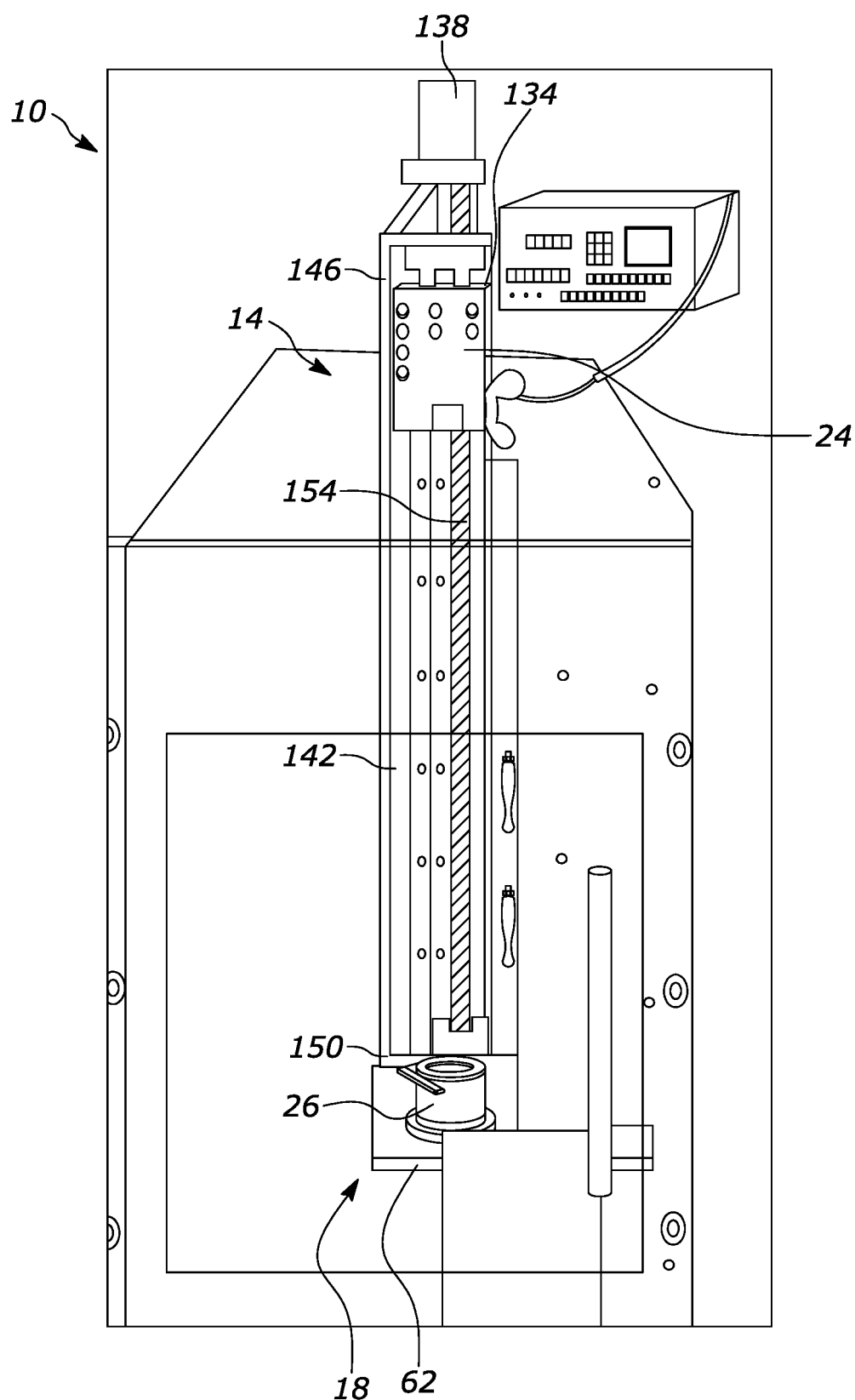
FIG. 14 is a partial, front view of the machine of FIG. 1, showing the linear mount in an initial position.
Figure 15:
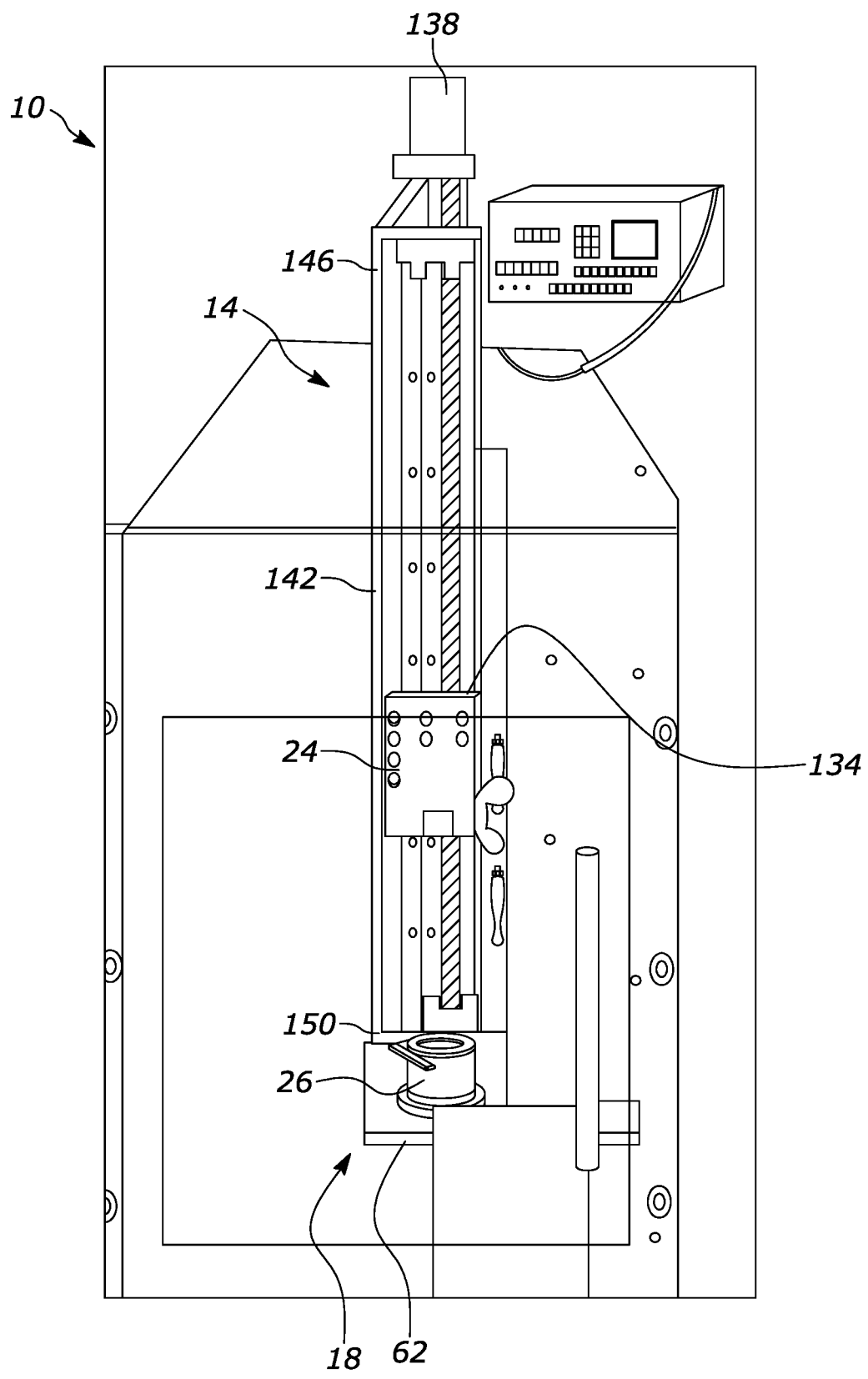
FIG. 15 is a partial, front view of the machine of FIG. 1, showing the linear mount in a first position.
Figure 16:
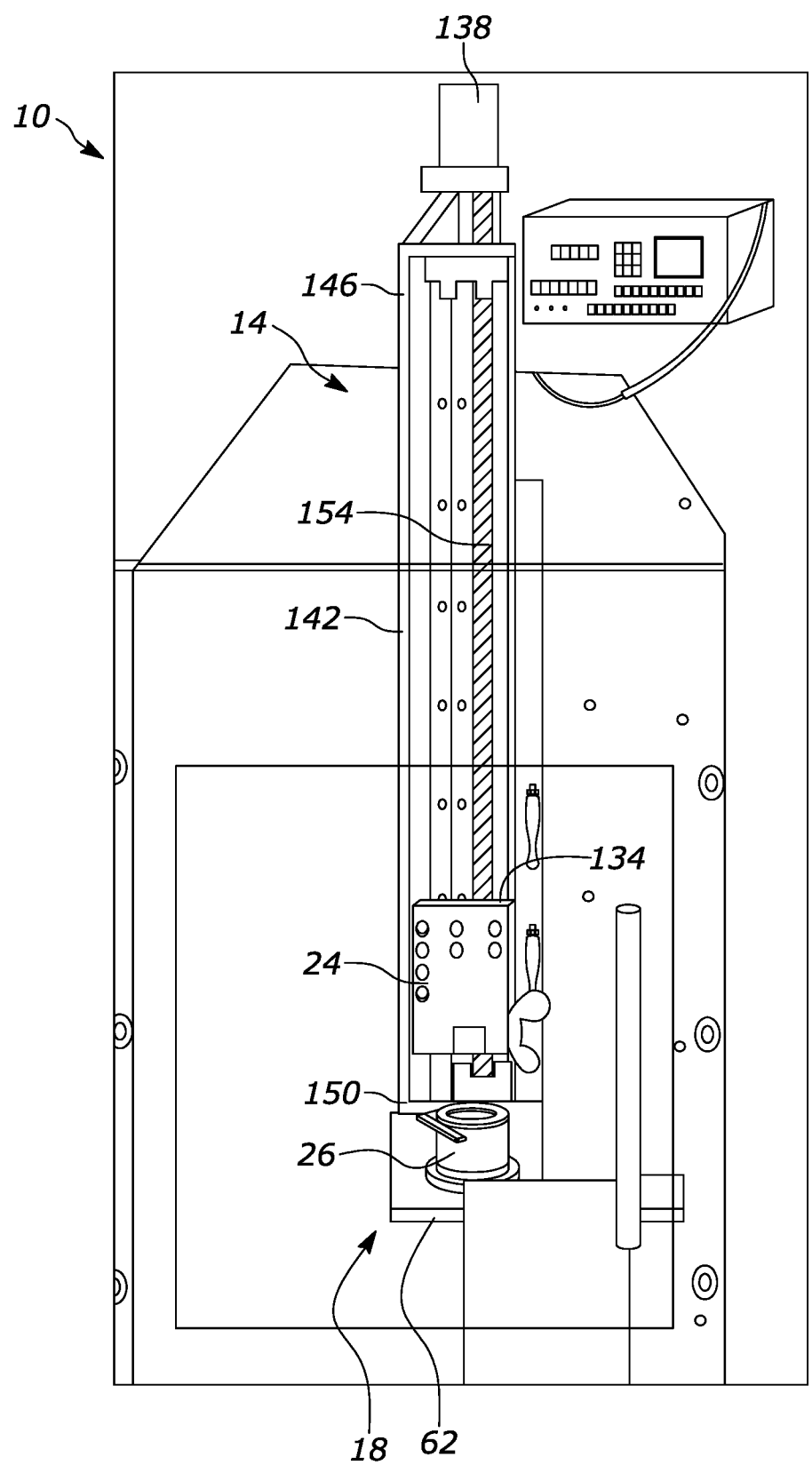
FIG. 16 is a partial, front view of the machine of FIG. 1, showing the linear mount in a second position.

The controller 22 is also programmed to receive three different positioning signals to move the linear mount 134 between the initial position, first position, and second position. Three buttons 200, 202, 204 for positioning the linear mount 134 are disposed on a front panel 232 of the control box 194. A first button 202 communicates with the controller 22 to move the linear mount 134 to a "HOME" or initial position, as shown in FIG. 14. A second button 204 communicates with the controller 22 to move the linear mount 134 to a "READY" or first position, as shown in FIG. 15. The controller 22 is programmed to receive a first position signal from the "READY" button 202, and then transmit a signal to the actuator 138 of the linear assembly 14 to move the linear mount 134 to the first position. A third button 204 communicates with the controller 22 to "GO" or to move the linear mount 134, at the set speed, to the second position as shown in FIG. 16. Particularly, the controller 22 is programmed to receive a second position signal from the "GO" button 204 and transmit a signal to the actuator 138 of the linear travel assembly 14 to move the linear mount 134 from the first position to the second position at the set speed. While the machine 10 is arranged to move the linear mount 134 along a vertically-oriented track 142, in another arrangement of the machine 10, the linear mount 134 may be disposed and movable along a horizontally-oriented track. In yet another example, the machine 10 may be arranged to move the CSTD fixture 24 by rotating the mount about a circular or curved track or path. In this case, the controller 22 may be programmed to move the CSTD fixture 24 and mount between initial, first, and second positions along a curved track or pathway.

The controller 22 of the illustrated example may be programmed to operate the machine 10 in six different configurations based on a combination of the linear travel and rotary assembly settings. In a first configuration, the linear mount 134 moves at a fast speed with no rotation of the vial mount 62. In a second configuration, the linear mount 134 moves at a slow speed with no rotation of the vial mount 62. In a third configuration, the linear mount 134 moves at a fast speed with the vial mount 62 rotating in one direction. In a fourth configuration, the linear mount 134 moves at a slow speed with the vial mount 62 rotating in one direction. In a fifth configuration, the linear mount 134 moves at a fast speed with the vial mount 62 rotating in two directions. Finally, in a sixth configuration, the linear mount 134 moves at a slow speed with the vial mount 62 rotating in two directions. In other examples, the controller 22 may be programmed to move the linear mount 134 at more than two speeds, to rotate the vial mount 62 at various speeds to create additional configurations of the machine 10.

Figure 17:
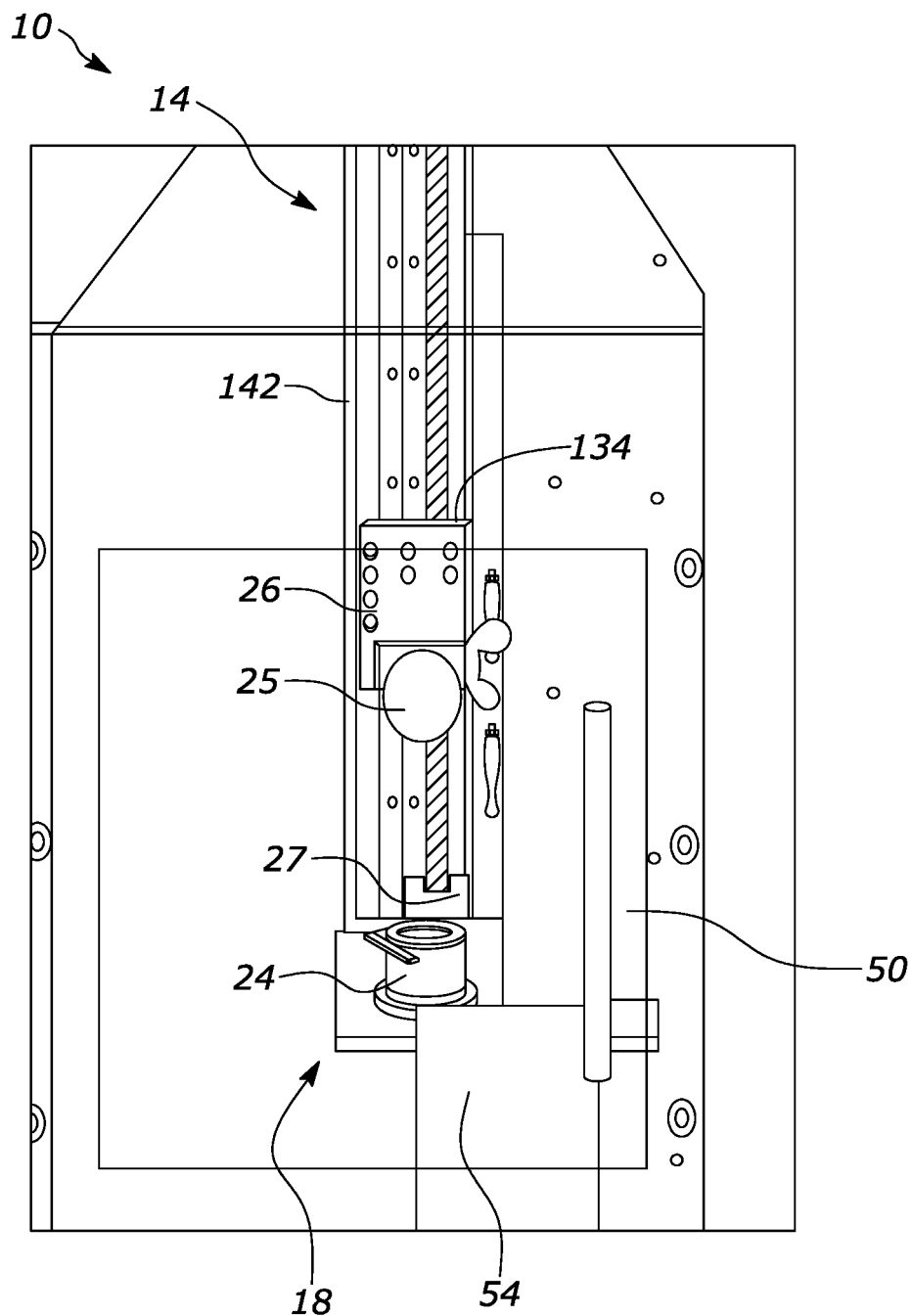
FIG. 17 is a partial, front view of the machine of FIG. 1 with a CSTD secured to the CSTD fixture and a vial secured to the vial fixture, showing the linear mount in the first position.
Figure 18:
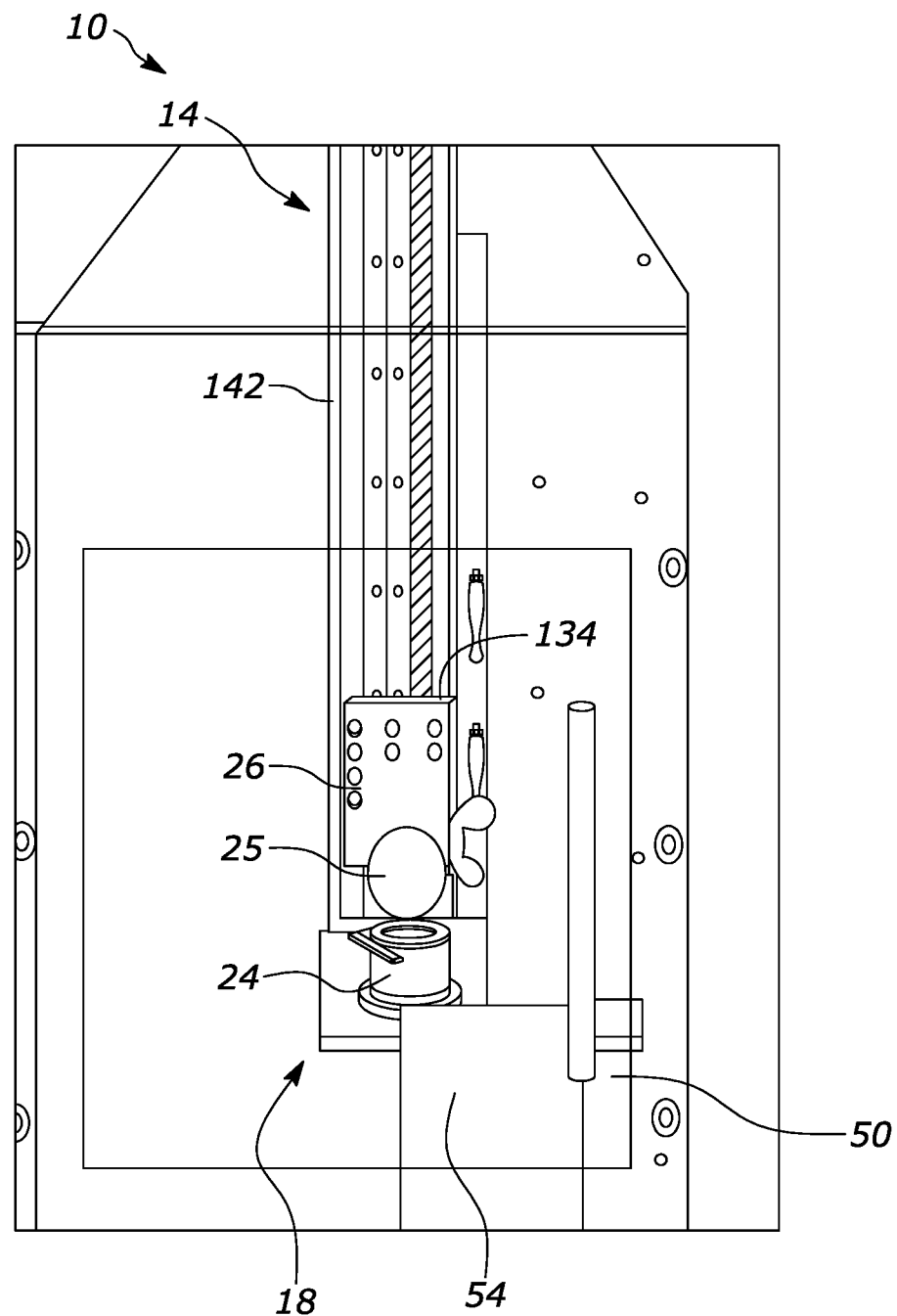
FIG. 18 is a partial, front view of the machine of FIG. 17, showing the linear mount in the second position.

Operation of the machine 10 will now be described with reference to the chronological sequence of the machine 10 shown FIGS. 17-19. The machine 10 is turned on by supplying power, and the "HOME" button 200 is pressed to move the linear mount 134 to the initial position (FIG. 14). An operator may then press the "READY" button 202, to move the linear mount 134 in the first position as shown in FIG. 17. In the first position, the machine 10 may be loaded with the CSTD fixture, CSTD, vial fixture, and vial by first unlocking the door 50 of the machine 10 by pressing the third switch 210 on the control box 194, and opening the door 50 to access the linear travel and rotary assemblies 14, 18. The method includes attaching a CSTD fixture 26 to the linear mount 134 of the linear travel assembly 14 of the machine 10. As shown in FIG. 10, this includes securing a plurality of fasteners 178 through bores 174 in the CSTD fixture 24 and bores 166 of the linear mount 134. The CSTD 25 is installed to the CSTD fixture 26 by placing a top portion of the CSTD 26 inside the aperture 184 of the CSTD fixture 26 and tightening the wing nut 186, securing the CSTD 27 to the fixture 26.

With the door 50 open, an operator may then install the vial fixture 26 to the rotatable base 82 of the rotary assembly 18. As shown in FIG. 5, installing the vial fixture 26 to the vial mount 62 includes securing a plurality of fasteners 90 through the bores 130 in the flange 110 of the fixture 26 and through the bores 94 of the rotatable base 82. The fixture 26 is rotated to a position so that the switch 66 is not pressed and the handle 106 of the fixture 26 is disposed approximately opposite the switch 66. A vial 27 is positioned in the fixture 26 and tightened by locking the handle 106. After both the CSTD 27 and vial 25 are secured to their respective fixtures 24, 26, the door 50 is closed and the third switch 210 may be pressed to lock the door 50. The machine 10 will not be operated unless the door 50 is fully closed and the lock 58 is activated.

At this point, an operator may select a linear speed (fast or slow) and rotary motion (neutral, one direction, two directions) by positioning the switches 206, 208 on the switch box 194 at desired settings. The operator may then press the "GO" button 204 to activate the linear travel assembly 14 to move the linear mount 134 from the first position to the second position. If the second switch 208 is pushed from center (away from neutral), pressing the "GO" button 204 also activates the rotary assembly 18 to begin rotating the vial fixture 24. As shown in FIG. 18, the linear mount 134 moves toward the second end 150 of the track 142 and a portion of the CSTD 25 engages with the vial 27 when the linear mount 134 is in the second position. The portion of the CSTD 25 that engages with the vial 27 may include the CSTD spike that is inserted into and/or through the vial stopper. For example, the CSTD 25 engages the vial 27 by piercing the stopper without the CSTD spike being fully inserted through the stopper of the vial 27. In another example, the CSTD spike may be fully inserted through the stopper but the top of the CSTD may not be completely locked to the rim of the vial 27.

Figure 19:
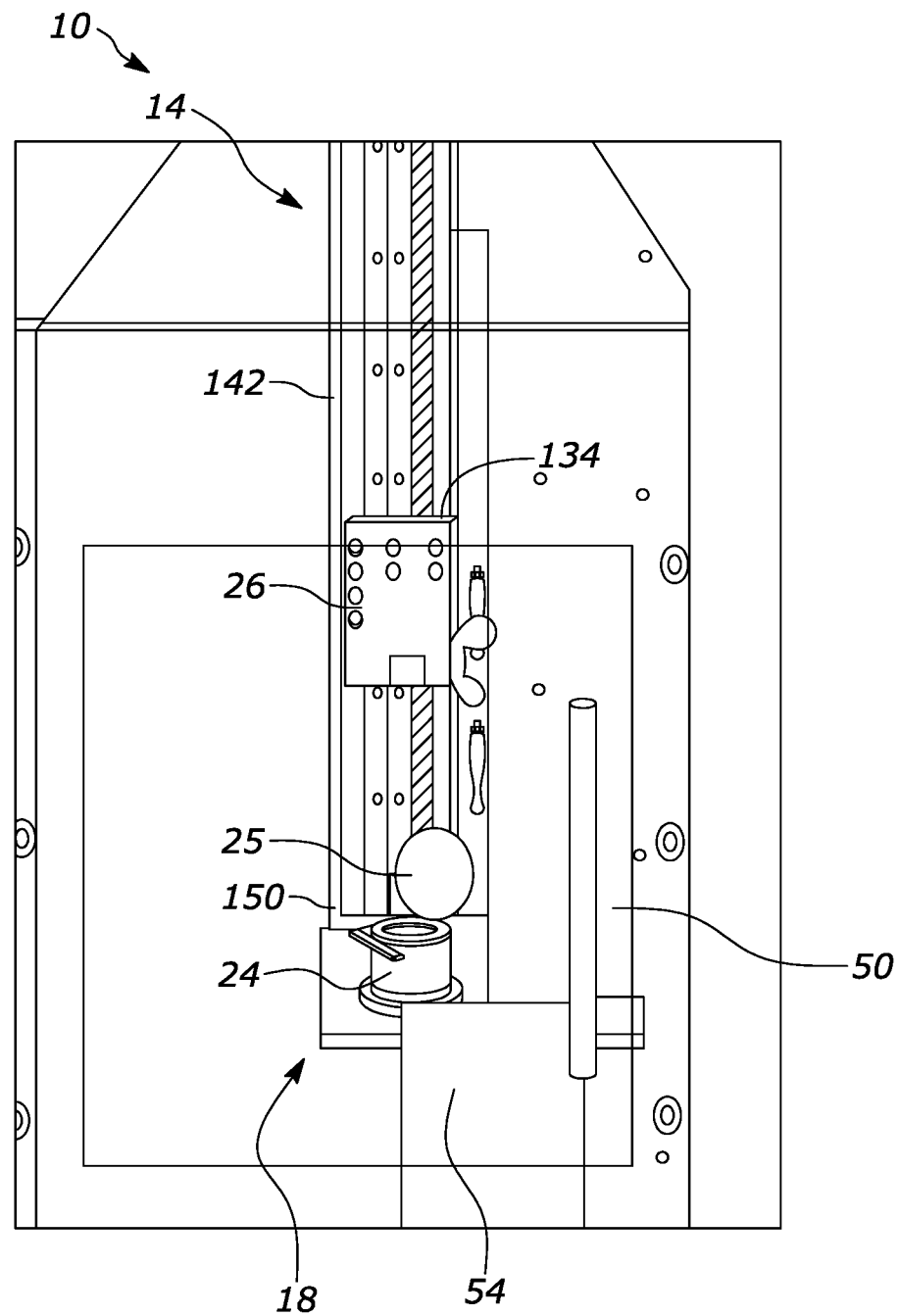
FIG. 19 is a partial, front view of the machine of FIG. 17, showing the linear mount in the first position with the CSTD removed from the CSTD fixture and coupled to the vial.

Finally, in FIG. 19, the operator may press the "READY" button 204 to move the linear mount 134 away from the CSTD and vial and back to the first position. In FIG. 19, the linear mount 134 is spaced away from the rotary assembly 18 and the CSTD 25 is at least partially coupled to the vial 27 so that the linear mount 134 separates from the CSTD 25 without also removing the CSTD 25 from the vial 27. In some cases, the CSTD 25 is coupled to the vial 27 and no further assembly may be needed. In other cases, the CSTD spike is inserted partially though the stopper and/or the CSTD top is not yet snapped onto the vial 27. In these cases, further assembly (e.g., pushing the CSTD in an axial direction) may be performed manually. The door 50 may then be unlocked and opened to remove the vial fixture 24 holding the attached CSTD 25 and vial 27. A final step includes pressing the CSTD 25 vertically and toward the vial 27 to complete assembly of the vial 27 and the CSTD 25. The CSTD 25 is not fully assembled onto the vial 27 by the machine 10 in some cases because of varying stopper thicknesses of the vial 27. For example, assembling tougher rubber stoppers may result in the CSTD 25 being 0.05 mm to 5 mm away from full assembly, depending on the height of the vial, and stack up tolerance of the cap and plastic CSTD mount. In some cases, CSTDs have grippers that snap to top of vials, and if not fully assembled, an operator may give the CSTD an additional push to snap into place. As such, the machine 10 is arranged to only partially assemble the CTSD 25 to the vial 27, and an operator may complete assembly manually. However, in other examples, the machine 10 may be arranged to completely assembly the CSTD 25 to the vial 27 without requiring further assembly.

As described above, the machine 10 is arranged to assemble a variety of different CSTDs to a variety of different size vials. To assemble the appropriate CSTD and vial, an operator may select the CSTD from a plurality of available and distinct CSTDs and corresponding CSTD fixture. Similarly, the operator may select the vial for assembling with the CSTD and the corresponding vial fixture. The machine 10 assembles CSTD onto various sized vials at different linear speed and rotational motions. For example, the CSTD fixture may be compatible with BD PhaSeal, Tevadaptor, ChemoClave, and Equashield or other CSTDs. The machine 10 assembles a variety of CSTDs to different sized vials, for example, 5 cc, 6R, and 10 cc vials, that may include a different types of stoppers.

The machine 10 provides at least six different testing configurations for a variety of different CSTD and vial combinations to accurately test and determine proper assembly and vial stopper properties to avoid stopper fragmentation and coring. The machine 10 provides consistency and removes human variants, such as fatigue, external forces, etc., to test all samples the same way and obtain true data. The machine 10 and method described herein may provide insight into design and/or improved assembly of CSTDs and vials to reduce instances of coring.

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:

1. A closed system transfer device (CSTD) and vial assembly machine, the machine comprising:
    a linear travel assembly including a linear mount, and an actuator operably coupled to the linear mount, the linear mount movable in an axial direction between a first position and a second position spaced from the first position;
    a CSTD fixture configured to be removably coupleable to the linear mount;
    a vial mount disposed adjacent to a portion of the linear travel assembly; and
    a vial fixture configured to be removably coupleable to the vial mount;
    wherein the vial fixture is sized to hold a vial in axial alignment with a portion of the CSTD fixture when the vial fixture is coupled to the vial mount and the CSTD fixture is coupled to the linear mount;
    wherein when the linear mount moves from the first position to the second position, the linear mount moves relative to the vial mount; and
    either:
    (a) a plurality of available and distinct CSTD fixtures, from which the CSTD fixture is selected, or
    (b) a plurality of available and distinct vial fixtures for holding various sized vials, from which the vial fixture is selected, or
    (c) a plurality of available and distinct vial inserts, from which a vial insert is selected and disposed in the vial fixture.

2. The machine of claim 1, further comprising a controller communicatively coupled with the linear travel assembly, the controller being programmed to move the linear mount to the first position and to move the linear mount to the second position.

3. The machine of claim 2, wherein the controller is communicatively coupled to the actuator of the linear travel assembly to change position of the linear mount.

4. The machine of claim 2, further comprising a rotary assembly including the vial mount and an actuator operably coupled with the vial mount to rotate the vial mount in one or more directions.

5. The machine of claim 4, wherein the controller is communicatively coupled with the rotary assembly and programmed to receive a first rotation signal to rotate the vial mount in a first direction, and to receive a second rotation signal to rotate the vial mount in the first direction and the second direction.

6. The machine of claim 4, wherein the controller is communicatively coupled to the actuator of the rotary assembly to rotate the vial mount in one or more directions.

7. The machine of claim 2, wherein the controller is programmed to receive a first signal to operate the actuator of the linear travel assembly to move the linear mount at a first speed and to receive a second signal to move the linear mount at a second speed different than the first speed.

8. The machine of claim 2, wherein the controller is programmed to (a) receive a first positioning signal to move the linear mount to the first position, (b) receive a second positioning signal to move the linear mount from the first position to the second position, and/or (c) move the linear mount to a third position spaced from the first position and the second position.

9. A method of assembling a closed system transfer device (CSTD) with a vial, the method comprising:
    attaching a CSTD fixture to a linear mount of a linear travel assembly of a machine, the linear travel assembly including the linear mount and an actuator operably coupled with the linear mount, the linear mount movable in an axial direction between a first position and a second position spaced from the first position;
    attaching a CSTD to the CSTD fixture;
    attaching a vial fixture to a vial mount of the machine, the vial mount disposed adjacent to a portion of the linear travel assembly;
    attaching a vial to the vial fixture, wherein the vial is in axial alignment with a portion of the CSTD;
    activating the linear travel assembly to move the linear mount from the first position to the second position;
    engaging a portion of the CSTD with the vial when the linear mount is in the second position; and
    either:
    (a) selecting the CSTD fixture from a plurality of available and distinct CSTD fixtures, or
    (b) selecting the vial fixture from a plurality of available and distinct vial fixtures, or
    (c) selecting a vial insert from a plurality of available and distinct vial inserts, and disposing the vial insert in the vial fixture.

10. The method of claim 9, further comprising receiving, via a controller, a first position signal to move the linear mount to the first position, wherein the controller is communicatively coupled to the actuator of the linear travel assembly.

11. The method of claim 10, further comprising receiving, via the controller, a second position signal to move the linear mount to the second position.

12. The method of claim 10, further comprising receiving, via the controller, (d) a first speed signal to move the linear mount at a first speed, and (e) a second speed signal to move the linear mount at a second speed, wherein the second speed is greater than the first speed.

13. The method of claim 10, wherein attaching the vial fixture to the vial mount includes securing the vial fixture to a rotary assembly of the machine, the rotary assembly including the vial mount and an actuator operably coupled to the vial mount.

14. The method of claim 13, further comprising receiving, via the controller, (d) a first rotation signal to rotate the vial fixture in a first direction, wherein the controller is communicatively coupled to the actuator of the rotary assembly, and (e) a second rotation signal to rotate the vial fixture in the first direction and the second direction, opposite the first direction.

15. The method of claim 9, further comprising (a) selecting the CSTD from a plurality of available and distinct CSTDs.

16. The method of claim 9, further comprising (a) selecting the vial from a plurality of available and distinct vials.

17. The method of claim 9, further comprising removing the CSTD and vial after the CSTD engages the vial and coupling the CSTD further with the vial.

* * * * *